(12) United States Patent
Aliyev et al.

(10) Patent No.: US 8,778,827 B2
(45) Date of Patent: *Jul. 15, 2014

(54) CATALYST COMPOSITION AND PROCESS FOR OLIGOMERIZATION OF ETHYLENE

(75) Inventors: Vugar Aliyev, Riyadh (SA); Mohammed Al-Hazmi, Riyadh (SA); Fuad Mosa, Riyadh (SA); Peter M. Fritz, Unterhaching (DE); Heinz Bölt, Wolfratshausen (DE); Anina Wöhl, Pullach (DE); Wolfgang Müller, Munich (DE); Florian Winkler, Munich (DE); Anton Wellenhofer, Hohenschäftlarn (DE); Uwe Rosenthal, Lambrechtshagen (DE); Bernd H. Müller, Rostock (DE); Marko Hapke, Rostock (DE); Normen Peulecke, Rostock (DE)

(73) Assignees: Saudi Basic Industries Corporation, Riyadh (SA); Linde AG (DE)

(*) Notice: Subject to any disclaimer, the term of this patent is extended or adjusted under 35 U.S.C. 154(b) by 537 days.

This patent is subject to a terminal disclaimer.

(21) Appl. No.: 12/734,770

(22) PCT Filed: Nov. 5, 2008

(86) PCT No.: PCT/EP2008/009305
§ 371 (c)(1), (2), (4) Date: Aug. 9, 2010

(87) PCT Pub. No.: WO2009/068157
PCT Pub. Date: Apr. 6, 2009

(65) Prior Publication Data
US 2010/0298618 A1  Nov. 25, 2010

(30) Foreign Application Priority Data

Nov. 28, 2007  (EP) .................................... 07023013

(51) Int. Cl.
*B01J 31/18*  (2006.01)
*C07C 2/32*  (2006.01)

(52) U.S. Cl.
USPC ........... 502/124; 502/118; 502/121; 502/123; 585/510; 585/511; 585/513; 585/520; 585/521; 585/522; 585/523

(58) Field of Classification Search
USPC ......... 585/502, 510, 511, 513, 520, 521, 522, 585/523; 502/102, 103, 118, 121, 123, 124, 502/117
See application file for complete search history.

(56) References Cited

U.S. PATENT DOCUMENTS

| | | | |
|---|---|---|---|
| 3,676,523 A | 7/1972 | Mason | |
| 3,906,053 A | 9/1975 | Lanier | |
| 3,969,269 A * | 7/1976 | Caunt | 502/121 |
| 4,668,838 A | 5/1987 | Briggs | |
| 5,563,312 A | 10/1996 | Knudsen | |
| 5,744,677 A | 4/1998 | Wu | |
| 5,750,817 A | 5/1998 | Tanaka | |
| 5,770,684 A * | 6/1998 | Stewart et al. | 528/392 |
| 5,811,681 A | 9/1998 | Braun et al. | |
| 5,968,866 A * | 10/1999 | Wu | 502/155 |
| 6,031,145 A | 2/2000 | Commereuc | |
| 6,184,428 B1 | 2/2001 | Zahoor | |
| 6,337,297 B1 * | 1/2002 | Mimura et al. | 502/117 |
| 6,800,702 B2 * | 10/2004 | Wass | 526/124.3 |
| 6,828,269 B2 | 12/2004 | Commereuc et al. | |
| 7,022,788 B2 * | 4/2006 | Wass | 526/172 |
| 7,273,959 B2 | 9/2007 | Drent | |
| 7,425,661 B2 | 9/2008 | McConville | |
| 8,258,501 B2 | 9/2012 | Werner et al. | |
| 8,329,608 B2 | 12/2012 | Knudsen et al. | |
| 2002/0035029 A1 | 3/2002 | Yoshida | |
| 2006/0293546 A1 | 12/2006 | Nabika | |
| 2007/0027350 A1 | 2/2007 | Nabika | |
| 2007/0129583 A1 | 6/2007 | De Boer | |
| 2007/0185357 A1 | 8/2007 | De Boer | |
| 2007/0185363 A1 | 8/2007 | Bercaw | |
| 2010/0190939 A1 | 7/2010 | Fritz et al. | |
| 2010/0298618 A1 | 11/2010 | Aliyev et al. | |

FOREIGN PATENT DOCUMENTS

| | | |
|---|---|---|
| GB | 1020563 A1 | 2/1966 |
| JP | 0699074 A | 4/1995 |
| JP | 2007169267 A | 7/2007 |
| WO | WO 9737765 A2 | 10/1997 |

(Continued)

OTHER PUBLICATIONS

Cotton, "Discovering and Understanding Multiple Metal-to-Metal Bonds" in Accounts of Chemical Research, 11(6), 225-232 (1978)—month unknown.*
Steiner, et al., "From Neutral Iminophosphoranes to Multianionic Phosphazenates. The Coordination Chemistry of Imino-Aza-P(V) Ligands" in Coordination Chemistry Reviews, 227 (2002), 193-216—month unknown.*
Jabri, Amir et al., "Isolation of a Cationic Chromium(II) Species in a Catalytic System for Ethylene Tri- and Tetramerization", Organometallics, ACS, Washington, D.C., US, vol. 25, No. 3, pp. 715-718 (Jun. 1, 2006).

(Continued)

*Primary Examiner* — In Suk Bullock
*Assistant Examiner* — Bradley Etherton
(74) *Attorney, Agent, or Firm* — Cantor Colburn LLP

(57) ABSTRACT

The present invention relates to a catalyst composition comprising: (a) a binuclear chromium(II) complex; (b) a ligand of the general structure (A) $R_1R_2P-N(R_3)-P(R_4)-N(R_5)-H$ or (B) $R_1R_2P-N(R_3)-P(R_4)-N(R_5)-PR_6R_7$, wherein $R_1$, $R_2$, $R_3$, $R_4$, $R_5$, $R_6$ and $R_7$ are independently selected from halogen, amino, trimethylsilyl, $C_1$-$C_{10}$-alkyl, aryl and substituted aryl, wherein the PNPN- or PNPNP-unit is optionally part of a ring system; and (c) an activator or co-catalyst, as well as to a process for oligomerization of ethylene.

20 Claims, No Drawings

(56) References Cited

FOREIGN PATENT DOCUMENTS

| WO | WO 0110876 A1 | 2/2001 |
| WO | WO 0183447 A2 | 2/2001 |
| WO | WO 0204119 A1 | 1/2002 |
| WO | WO 03004158 A2 | 1/2003 |
| WO | 03053891 A1 | 7/2003 |
| WO | 2004056478 A1 | 7/2004 |
| WO | 2006108803 A1 | 10/2006 |
| WO | 1574492 A2 | 5/2007 |

OTHER PUBLICATIONS

Cotton, F et al., "Advanced inorganic chemistry", Wiley-Interscience, New York, US, pp. 683-686.

Wrackmeyer, Bernd et al., "The first 1, 3, 2-diazaphospha-[3]ferrocenophanes", Inorganic Chemistry Communications, 7(7), pp. 884-888.

Burford, Neil et al., "Sequential dehydrochloride coupling of trichlorophosphine with 2, 6-di-isopropylaniline: aminophosphine precursors to phosphetidiness", Canadian Journal of Chemistry, 80(11), pp. 1404-1409 (Oct. 7, 2002).

Scherer, Otto J. et al., "Synthesis and isolation of cis- and trans-1,3,2.lambda.3,4.lambda.3-diazadiphosphetidine", Angewandte Chemie Int. Ed. Engl., vol. 15, No. 12, p. 772 (1976).

Katz, Stephanie A. et al., "Diastereoselectivity in the Formation of Skeletally Stabilized Phosphazanes", Inorganic Chemistry, 33(9), pp. 1762-1769 (1994).

Helm, Monte L. et al., "Synthesis, Characterization, and Solution Properties of Skeletally Stabilized Triphosphazanes", Inorganic Chemistry, 38(13), pp. 3167-3172.

Mundt, Cornelia et al., "N-Phosphanylated 1,3,2-oxaza- and 1,3,2-diazaphospholanes and phosphorinanes", Phosphorus, Sulfur and Silicon and the Related Elements, 88(1-4), pp. 75-81 (1994).

European Patent No. 1574492 (A2); Publication Date: Sep. 14, 2005; Abstract Only; 2 Pages.

Dixon et al.; "Advances in Selective Ethylene Trimerisation—A Critical Overview"; Journal of Organometallic Chemistry; vol. 689; 2004; pp. 3641-3668.

Eichhorn et al.; "(N-lithioamino)diorganophosphanes and Bis(n-Lithioamino)organophosphanes: Synthesis and Structures"; Eur. J. Inorg. Chem.; 1999; pp. 2355-2368.

International Search Report; International Application No. PCT/EP2008/009305; International Filing Date: Nov. 5, 2008; Date of Mailing: Jan. 7, 2009; 5 Pages.

Written Opinion of the International Searching Authority; International Application No. PCT/EP20081009305; International Filing Date: Nov. 5, 2008; Date of Mailing: Jan. 7, 2009; 11 Pages.

Wass, Duncan F.; "Chromium-Catalysed Ethene Trimerisation and Tetramerisation—Breaking the Rules in Olefin Oligomerisation"; Dalton Transaction; 2007; pp. 816-819.

English Abstract of Japanese Patent No. 0699074(A); Publication Date Apr. 12, 1994; 2 pages.

English Abstract of Japanese Patent No. 2007169267A; Publication Date Jul. 5, 2007; 2 pages.

\* cited by examiner

CATALYST COMPOSITION AND PROCESS FOR OLIGOMERIZATION OF ETHYLENE

The present invention relates to a catalyst composition and a process for the oligomerization of ethylene.

Linear alpha-olefins (LAOs) are very useful intermediates for the manufacture of detergents, synthetic lubricants, copolymers, plasticizer alcohols and many other important products. There are several producers of such LAOs via oligomerization of ethylene, e.g. SHELL, BP, SABIC, AMOCO, CHEVRON PHILIPS etc. An intrinsic problem of all of these metal-catalyzed ethylene oligomerization processes is the production of LAO mixtures following a mathematical distribution (Schulz-Flory or Poisson), which is difficult to separate and whose composition often does not match market demands. To solve this technical and economical unsatisfying situation, there is a deep interest to overcome the technical limitations and to transform the non-selective ethylene oligomerization reactions into more selective processes. Recently these activities are predominantly concentrated on the selective trimerization of ethylene to 1-hexene (review: D. H. Morgan et al. J. Organomet. Chem. 2004, 689, 3641; and refs. Cited therein) as well as the selective tetramerization of ethylene to 1-octene (recent review: D. Wass, Dalton Trans. 2007, 816).

Several patents for the trimerization of ethylene to 1-hexene and the tetramerization of ethylene to 1-octene are already known. In most of these cases different chromium precatalysts in combination with a broad array of different ligand systems and activating agents (like main group metal alkyl compounds) were utilized.

Prior art chromium based ethylene trimerization catalyst with chromium compounds, organoaluminum activators and different ligands are those listed e.g. in the following patent publications: U.S. Pat. No. 4,668,838; EP 0 668 105; U.S. Pat. No. 5,750,817; U.S. Pat. No. 6,031,145; U.S. Pat. No. 5,811,681; EP 537609; EP 1574492; US 2004783429; WO 2005039758; FR 2833191; US 2002035029; WO 2002004119; WO 2001083447 and EP 1110930. Here, various chelating and non-chelating donor ligands and a large number of Cr(III) precursor complexes were claimed. In WO 2003004158, Cr(II) complexes such as chromium(II)acetate were claimed in conjunction with substituted cyclopentadienes as suitable ligand systems, in addition to the already described and utilized Cr(III) complexes. In WO 2003053891, also Cr(II) complexes such as, e.g., chromium (II) acetate are claimed. The claimed ligands are bis(2-diphenylphosphino-ethyl)amines and derivatives thereof.

Prior art ethylene tetramerization catalysts include a number of different transition metal compounds, organoaluminum activators or different ligands, that have been used in the same or slightly modified form for the trimerization process. Patents concerning the tetramerization are: U.S. Pat. No. 6,184,428; U.S. Pat. No. 3,676,523; DE Patent 14 43 927; U.S. Pat. No. 3,906,053; WO 2005/086251; WO 2006108803, WO 2006099053, WO 2007057455, WO 2007057458 and WO 2007088329. In most of these patents, the obtained mixture of olefins does not contain more than 25 weight-% 1-octene. In some of the most recent applications, different PNP- and similar chelating donor ligands were claimed in conjunction with Cr(III) complexes only (WO 2004/056478 and WO 2004/056479). These applications were the first to demonstrate that in ethylene oligomerization a high selectivity towards 1-octene (up to 70 mass-%) with significantly less simultaneous 1-hexene production can be achieved. It was pointed out that the formed nine-membered ring systems (chromacyclononane) are the reason for the selective tetramerization of ethylene to 1-octene with 70% mass selectivity.

The selective ethylene trimerization and tetramerization catalysts and processes known generally have to cope with some disadvantages. The catalysts show only low selectivities to the desired products 1-hexene and/or 1-octene due to by-products from side reaction channels. Further limited purities of the products are obtained, i.e. the selectivities within the specific $C_6$- or $C_8$-cut due to isomerization, branched olefin formation, etc. Also wax formation, i.e. formation of heavy, long-chain, high carbon-number products is detected. This is also true for polymer formation (polyethylene, branched and/or cross-linked polyethylene) leading to considerable product yield loss and fouling of equipment. Further it has to be mentioned that prior art processes only show poor turnover rates and catalyst activity resulted in high cost per kg product. Prior art catalysts and ligands are usually to be prepared with high costs. Ligands are usually difficult to synthesize, resulting in poor availability and high catalyst cost. The catalyst performance is highly susceptible to trace impurities, and the catalyst components are often difficult to handle in technical environment. The prior art processes usually require harsh reaction conditions, i.e. high temperatures and pressures, resulting in high invest, maintenance and energy costs. Finally, high costs are also to be expected for co-catalyst/activator.

It is therefore an object of the present invention to overcome the difficulties of the prior art and to provide a catalyst composition showing improved selectivities and purities in the oligomerization of ethylene without formation of wax or polymer, showing rather improved turnover rates with fair costs for preparing catalyst and ligand.

Additionally, a process for the oligomerization of ethylene shall be provided.

The first object is achieved by a catalyst composition comprising: (a) a binuclear chromium(II) complex; (b) a ligand of the general structure (A) $R_1R_2P-N(R_3)-P(R_4)-N(R_5)-H$ or (B) $R_1R_2P-N(R_3)-P(R_4)-N(R_5)-PR_6R_2$, wherein $R_1$, $R_2$, $R_3$, $R_4$, $R_5$, $R_6$ and $R_7$ are independently selected from halogen, amino, trimethylsilyl, $C_1$-$C_{10}$-alkyl, aryl and substituted aryl, wherein the PNPN- or PNPNP-unit is optionally part of a ring system; and (c) an activator or co-catalyst.

As is to be understood, any cyclic derivatives of (A) and (B) can be utilized as ligand, wherein at least one of the P or N atoms of the PNPN-unit (structure (A)) or PNPNP-unit (structure (B)) is a ring member, the ring being formed from one or more constituent compounds of structures (A) or (B) by substitution, i.e. by formally eliminating per constituent compound either two whole groups $R_1$-$R_7$ (as defined) or H, one atom from each of two groups $R_1$-$R_7$ (as defined) or a whole group $R_1$-$R_7$ (as defined) or H and an atom from another group $R_1$-$R_7$ (as defined), and joining the formally so-created valence-unsaturated sites by one covalent bond per constituent compound to provide the same valence as initially present at a given site.

Preferably, the chromium complex has a Cr—Cr-bond or two chromium centres are connected via a bridging ligand.

Most preferably, the binuclear chromium complex is selected from:

1
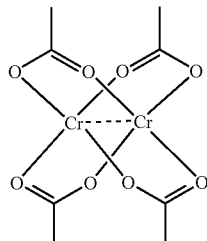

2
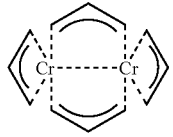

3
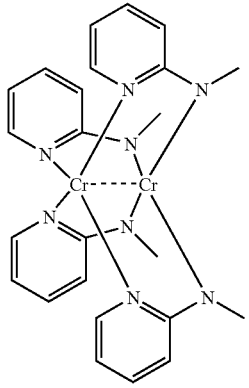

4
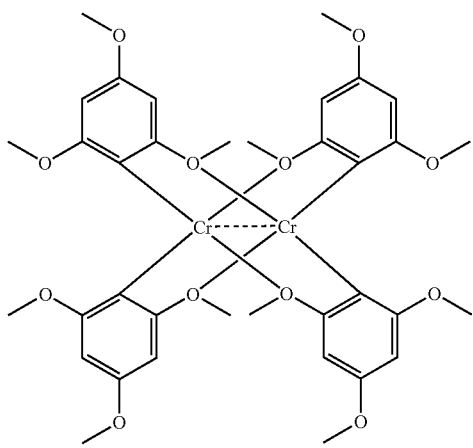

5
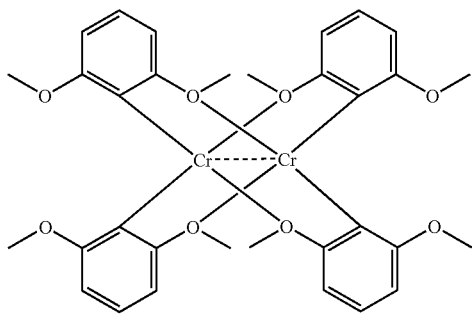

6
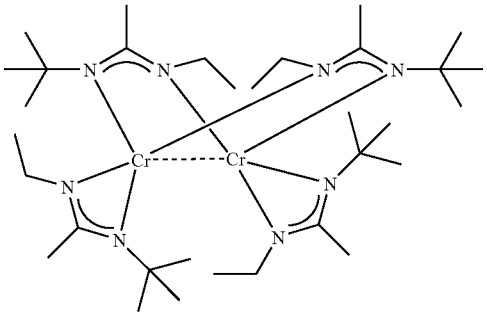

7
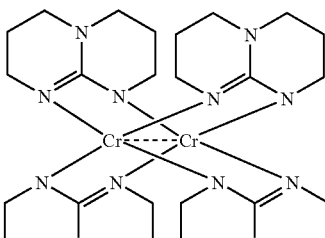

8
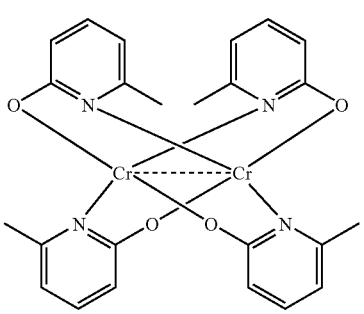

In one embodiment, $R_1$, $R_2$, $R_3$, $R_4$, $R_5$, $R_6$ and $R_7$ are selected from chloro, amino, trimethylsilyl, methyl, ethyl, isopropyl, tert-butyl, phenyl, benzyl, tolyl and xylyl.

In another embodiment, the activator or co-catalyst is selected from trimethyl aluminium, triethyl aluminium, tri-isopropylaluminum, triisobutyl aluminium, ethylaluminum sesquichloride, diethylaluminum chloride, ethyl aluminium dichloride, methylaluminoxane (MAO) or mixtures thereof.

The ligand may be selected from $(Ph)_2P$—N(i-Pr)—P($CH_3$)—N(i-Pr)—H, $(Ph)_2P$—N(i-Pr)—P(Ph)—N(i-Pr)—H, $(Ph)_2P$—N(i-Pr)—P(Ph)—N(Ph)—H, $(Ph)_2P$—N(i-Pr)—P(Ph)—N(tert-butyl)-H and $(Ph)_2P$—N(i-Pr)—P(Ph)—N(CH($CH_3$)(Ph))—H.

Preferably, the catalyst composition comprises a solvent, which may be selected from aromatic hydrocarbons, straight-chain and cyclic aliphatic hydrocarbons, straight-chain olefins and ethers, preferably toluene, benzene, ethyl benzene, cumene, xylenes, mesitylene, hexane, octane, cyclohexane, methylcyclohexane, hexene, heptene, octene, diethylether or tetrahydrofurane or mixtures thereof, most preferably toluene.

A second object of the invention is achieved by a process for oligomerization of ethylene, comprising subjecting a catalyst composition according to the invention to a gas phase of ethylene in a reactor and conducting an oligomerization.

Preferably, the oligomerization is carried at a pressure of 1 to 200 bar, preferably 10 to 50 bar.

Also preferred, the oligomerization is carried at a temperature of from 10 to 200° C., preferably 20 to 100° C.

In one embodiment, the process is carried out continuously, semi-continuously or discontinuously.

The mean residence time may be from 10 minutes to 20 hours, preferably 1 to 4 hours.

Most preferred, the process is a trimerization or tetramerization.

Surprisingly it was found that a process for oligomerization of ethylene utilizing the inventive catalyst composition avoids the broad spectrum of LAO products and allows for the selective production of the economically most desired products, namely 1-hexene and 1-octene. Unprecidented high selectivity, purity and sufficiently high active/turnover frequency are achieved.

The current invention is based on the fact that the selective tetramerization of ethylene to 1-octene and the trimerization of ethylene to 1-hexene can proceed more efficiently by using a binuclear transition metal complex, rather than a mononuclear transition metal complex, whose mechanism involves mononuclear metallocyclononanes and metallacycloheptanes, respectively.

Without wishing to be bound to any theory, it is assumed that for the binuclear chromium complexes utilized in a tetramerization reaction a mechanism is suggested wherein the reaction proceeds via metallocyclopentanes which the $C_4$-chain dimerizes to a saturated $C_8$-chain between the metal centers as illustrated in the following scheme:

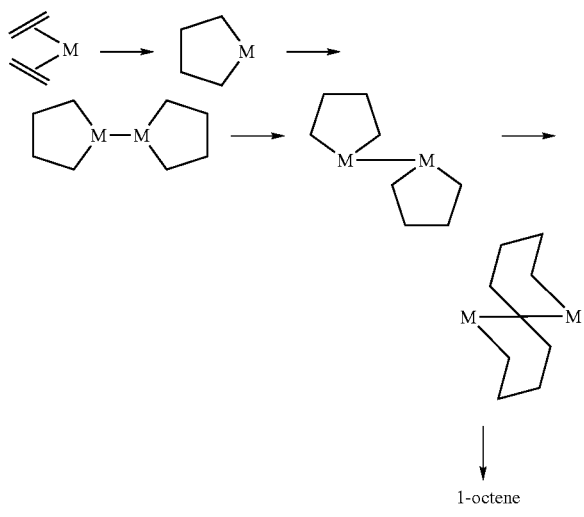

1-octene

The above mechanism is characterized by the novel principle of a dinuclear reductive elimination from chromium(II) via chromium(I) to chromium(0) leading to 1-octene.

The catalyst composition according to the present invention can be tuned by suitable ligands to the novel principle of dinuclear reductive elimination from chromium(0) via chromiumI) to chromium(0) (case: neutral ligands) or from chromium(I)/(II) via chromium(II)/(I) to chromium(I)/(0) (case: anionic ligands) leading selectively to 1-hexene:

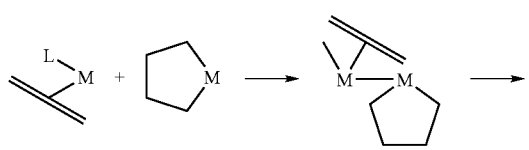

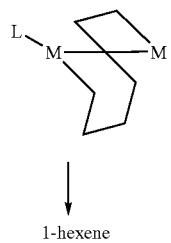

1-hexene

Additionally, it was surprisingly found that the modification of a tridentate ligand, such as (phenyl)$_2$P—N(isopropyl)-P(phenyl)$_2$ by an additional NH(isopropyl) unit resulted in the tetradentate ligand ((phenyl)$_2$PN(isopropyl)P(phenyl)NH(isopropyl)). Utilizing the former ligand in the catalyst composition resulted in a high selectivity towards the tetramerization of ethylene, whereas the latter ligand resulted in a high selectivity for the trimerization or tetramerization of ethylene depending on the substituents, as will be shown below in the examples section.

In other words, the inventive process results in the production of 1-octene and 1-hexene with high turnover rate and selectivity. An easy switchover from 1-octene to 1-hexene production by using specific ligands can be easily obtained. Further, a high reproduceability is obtained, e.g. the catalyst system is stable against interference from impurities and fluctuations in process conditions. Formation of wax and polymers is well suppressed. Additionally, in the inventive process slight reaction conditions may be employed, consequently resulting in low investive costs for technical-scale plant and low energy and operation costs.

Additional advantages and features of the present invention will become apparent from the following detailed description on the basis of examples.

A ligand to be used in the inventive catalyst composition may be prepared as follows:

Preparation of Ph$_2$PN(i-Pr)PMeNH(i-Pr): 2.21 g of Ph$_2$PCl (10 mmol) was slowly added to a mixture of 1.62 g MeP(NH(i-Pr))$_2$ (10 mmol) (Eur. J. Inorg. Chem. 1999, 12, 2355-68) and 5 ml triethylamine in 15 ml toluene at 0° C. The solution was stirred for additional 2 h at r.t. and then filtered to remove the amine-hydrochloride. After evaporation of the volatile compounds in vacuo a sticky oil remained. Yield: 80%

$^{31}$P-NMR(C$_6$D$_6$); 33.7, 57.6 (broad)

TRIMERIZATION BY BINUCLEAR COMPLEXES

Example 1

Ethylene trimerization using {[(i-Pr)$_2$N]Cr[μ-(i-Pr)$_2$N]}$_2$, ((phenyl)$_2$PN(isopropyl)P(phenyl)NH(isopropyl)) and triethylaluminum A 300 ml pressure reactor, equipped with dip tube, thermowell, gas entrainment stirrer, cooling coil, control units for temperature, pressure and stirrer speed (all hooked up to a data acquisition system) was inertized with dry argon and filled with 100 ml anhydrous toluene. Then 81.7 mg (0.2 mmol) of ((phenyl)$_2$PN(isopropyl)P(phenyl)NH(isopropyl)) in 10 ml toluene was combined with 65.6 mg {[(i-Pr)$_2$N]Cr[μ-(i-Pr)$_2$N]}$_2$ (0.13 mmol) under an argon blanket. This catalyst solution was transferred to the reactor under constant argon flow, along with 3.6 ml of a 1.9 mol/l solution of triethylaluminium in toluene.

The reactor was sealed, pressurized with 30 bar dry ethylene and heated to 50° C. While stirring at 1200 rpm, the ethylene comsumption was monitored by the data acquisition system and an electronic balance by constantly weighing the ethylene pressure cylinder. After 120 min residence time, the reaction in the liquid phase was quenched by transferring the liquid inventory by means of the ethylene pressure to a glass vessel filled with approx. 100 ml of water. The entire gas phase from the reactor's head space was quantified by a calibrated gas meter and was then collected quantitatively in a purged and evacuated gas bag.

After separation of the liquid organic phase, the total mass was determined by weighing. Subsequently, the composition of the organic phase was analyzed separately by GC/FID. Based on the measured data, the mass balance was closed and the overall yields and selectivities were determined. The product distribution of this example is summarized in Table 1.

Comparative Example 2

Ethylene trimerization using $CrCl_3$(tetrahydro-furane)$_3$, ((phenyl)$_2$PN(isopropyl)P(phenyl)NH(isopropyl)) and triethylaluminum In analogy to Example 1 a 300 ml pressure reactor was filled with 100 ml anhydrous toluene. A solution of 81.7 mg (0.2 mmol) of ((phenyl)$_2$PN(isopropyl)P(phenyl)NH(isopropyl)) in 10 ml toluene was combined with 50.0 mg (0.13 mmol) $CrCl_3$(tetrahydrofuran)$_3$ under a argon blanket. This catalyst solution was transferred to the reactor along with 3.6 ml of a 1.9 mol/l solution of triethlaluminium in toluene. The reactor was sealed, pressurized with 30 bar dry ethylene and heated to 50° C. After 120 min residence time while stirring at 1200 rpm the reaction mixture was worked up and analyzed as mentioned above. The product distribution of this example is summarized in Table 1.

The comparison shows higher activity for binuclear complexes.

TABLE 1

Ethylene trimerization runs

| Example | Activity, kg prod./g Cr | $C_6$-Yield, wt % | $C_8$-Yield, wt % | 1-hex in $C_6$ |
|---|---|---|---|---|
| 1 | 145 | 88 | 1 | 99.0 |
| 2 | 34 | 89 | 1 | 99.0 |

Tetramerization by Binuclear Compounds

Example 3

Ethylene tetramerization using {[(i-Pr)$_2$N]Cr[μ-(i-Pr)$_2$N]}$_2$, ((phenyl)$_2$PN(isopropyl)P(methyl)NH(isopropyl)) and triethylaluminum In analogy to Example 1 a 300 ml pressure reactor was filled with 100 ml anhydrous toluene and a solution of 69.3 mg of ((phenyl)$_2$PN(isopropyl)P(methyl)NH(isopropyl)) (0.2 mmol) in 10 ml toluene together with 65.6 mg {[(i-Pr)$_2$N]Cr[μ-(i-PO$_2$N]}$_2$ (0.13 mmol). After adding 3.6 ml of a 1.9 M solution of triethylaluminum in toluene the reactor was sealed, pressurized with 30 bar dry ethylene and heated to 50° C. After 120 min residence time while stirring at 1200 rpm the reaction mixture was worked up and analyzed as mentioned above. The product distribution of this example is summarized in Table 2.

Comparative Example 4

Ethylene oligomerization using $CrCl_3$(tetrahydrofuran)$_3$, ((phenyl)$_2$PN(isopropyl)P(methyl)NH(isopropyl)) and triethylaluminum In analogy to Example 1 a 300 ml pressure reactor was filled with 100 ml anhydrous toluene and a solution of 69.3 mg of ((phenyl)$_2$PN(isopropyl)P(methyl)NH(isopropyl)) (0.2 mmol) in 10 ml toluene together with 50.0 mg $CrCl_3$(tetrahydrofuran)$_3$ (0.13 mmol). After adding 3.6 ml of a 1.9 M solution of triethylaluminum in toluene the reactor was sealed, pressurized with 30 bar dry ethylene and heated to 50° C. After 120 min residence time while stirring at 1200 rpm the reaction mixture was worked up and analyzed as mentioned above. The product distribution of this example is consistent with a Schulz-Flory distribution and summarized in Table 2.

TABLE 2

Ethylene tetramerization runs

| Example | Activity, kg prod./g Cr | $C_6$-Yield, wt % | $C_8$-Yield, wt % | 1-hex in $C_6$ | 1-oct in $C_8$ |
|---|---|---|---|---|---|
| 3 | 21 | 8 | 82 | 98.0 | 98.0 |
| 4 | 33 | 30 | 28 | 98.0 | 98.0 |

As can be seen from the examples, by changing the ligand utilized in the catalyst composition an easy switch from trimerization (Example 1 and 2) to tetramerization (Example 3) may be achieved. Furthermore by using binuclear chromium (II) complexes an easy switch from unselective oligomerization (Example 4) to tetramerization (Example 3) is possible.

The features disclosed in the foregoing description and in the claims may, both separately and in any combination thereof, be material for realizing the invention in diverse forms thereof.

The invention claimed is:

1. A catalyst composition comprising:
   (a) a binuclear chromium(II) complex;
   (b) a ligand of the general structure
      (A) $R_1R_2P$—N($R_3$)—P($R_4$)—N($R_5$)—H or
      (B) $R_1R_2P$—N($R_3$)—P($R_4$)—N($R_5$)—P$R_6R_7$,
      wherein $R_1$, $R_2$, $R_3$, $R_4$, $R_5$, $R_6$ and $R_7$ are independently selected from halogen, amino, trimethylsilyl, $C_1$-$C_{10}$-alkyl, aryl and substituted aryl; and
   (c) an activator or co-catalyst.

2. The catalyst composition according to claim 1, wherein the binuclear chromium complex has a Cr—Cr-bond or two chromium centers connected via a bridging ligand.

3. The catalyst composition according to claim 2, wherein the binuclear chromium complex is selected from:

1 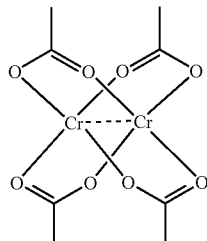

2 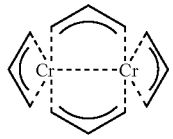

3 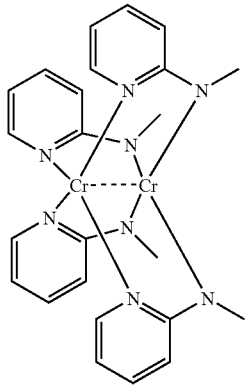

4 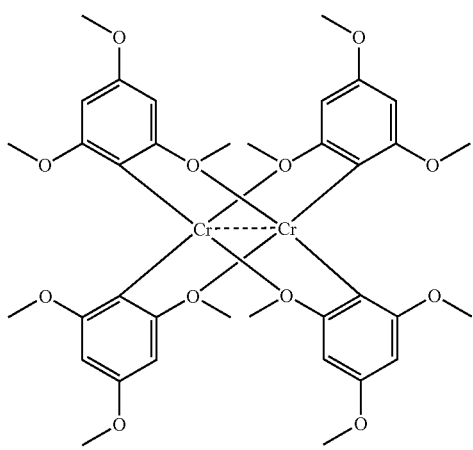

5 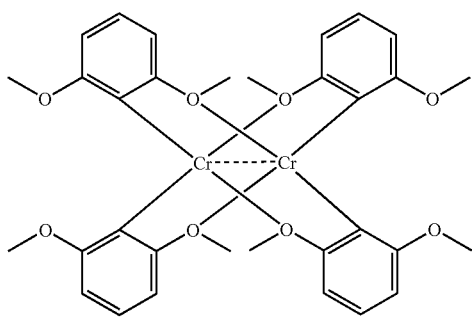

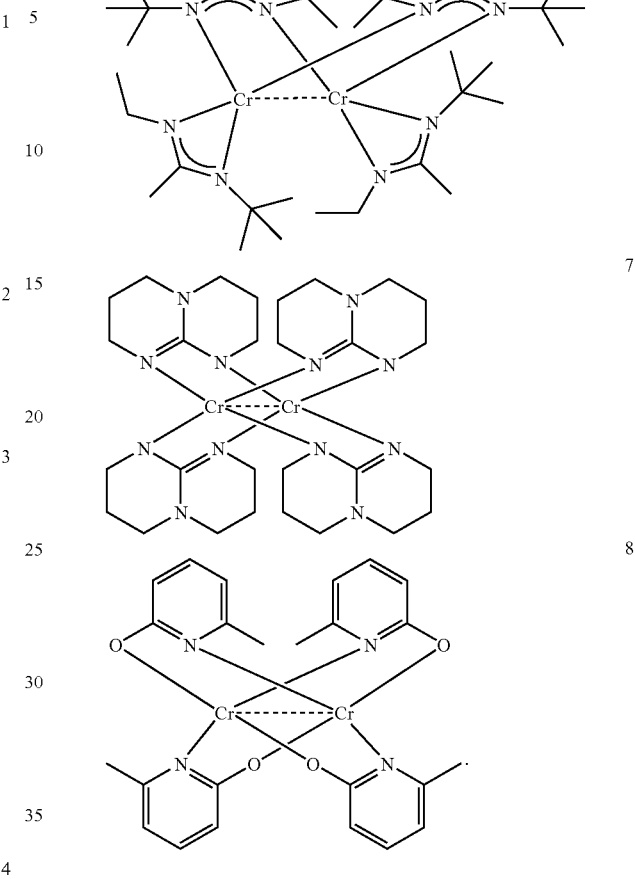

4. The catalyst composition according to claim 3, wherein $R_1, R_2, R_3, R_4, R_5, R_6$ and $R_7$ are selected from chloro, amino, trimethylsilyl, methyl, ethyl, isopropyl, tert-butyl, phenyl, benzyl, tolyl and xylyl.

5. The catalyst composition according to claim 4, wherein the activator or co-catalyst is selected from trimethyl aluminium, triethyl aluminium, triisopropyl aluminum, triisobutyl aluminium, ethylaluminum sesquichloride, diethylaluminum chloride, ethyl aluminium dichloride and methylaluminoxane (MAO), or mixtures thereof.

6. The catalyst composition of claim 5, further comprising a solvent selected from the group consisting of aromatic hydrocarbons, straight-chain and cyclic aliphatic hydrocarbons, straight-chain olefins and ethers, toluene, benzene, ethyl benzene, cumene, xylenes, mesitylene, hexane, octane, cyclohexane, methylcyclohexane, hexene, heptene, octene, diethylether and tetrahydrofurane, or mixtures thereof.

7. The catalyst composition of claim 6, wherein the PNPN or the PNPNP unit in the ligand is part of a ring system.

8. The catalyst composition according to claim 2, wherein the ligand is selected from $(Ph)_2P$—$N(i\text{-}Pr)$—$P(CH_3)$—$N(i\text{-}Pr)$—H, $(Ph)_2P$—$N(i\text{-}Pr)$—$P(Ph)$—$N(i\text{-}Pr)$—H, $(Ph)_2P$—$N(i\text{-}Pr)$—$P(Ph)$—$N(Ph)$—H, $(Ph)_2P$—$N(i\text{-}Pr)$—$P(Ph)$—$N(\text{tert-butyl})$-H and $(Ph)_2P$—$N(i\text{-}Pr)$—$P(Ph)$—$N(CH(CH_3)(Ph))$—H.

9. The catalyst composition according to claim 8, further comprising a solvent selected from the group consisting of aromatic hydrocarbons, straight-chain and cyclic aliphatic hydrocarbons, straight-chain olefins and ethers, toluene, benzene, ethyl benzene, cumene, xylenes, mesitylene, hexane, octane, cyclohexane, methylcyclohexane, hexene, heptene, octene, diethylether and tetrahydrofurane, or mixtures thereof.

10. The catalyst composition according to claim 9, wherein the solvent is toluene.

11. A process for oligomerization of ethylene, comprising contacting ethylene with a catalyst composition according to claim 9, at a temperature of from 20 to 100° C. and a pressure from 10 to 50 bar.

12. The process according to claim 11, wherein the binuclear chromium complex is selected from:

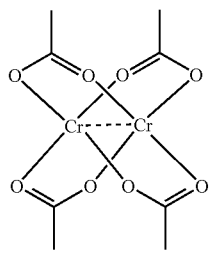

1

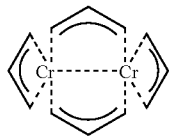

2

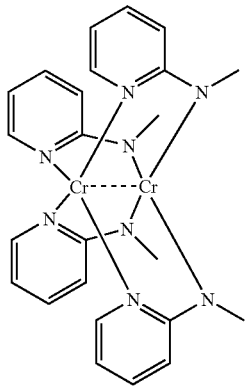

3

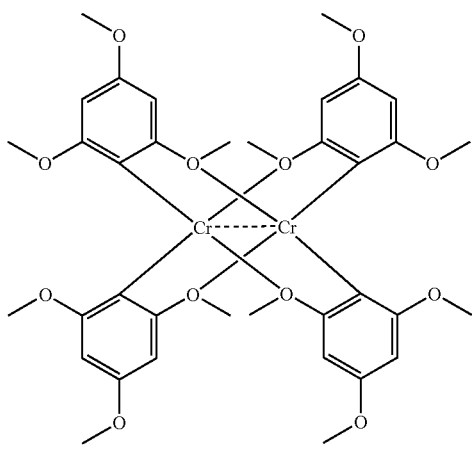

4

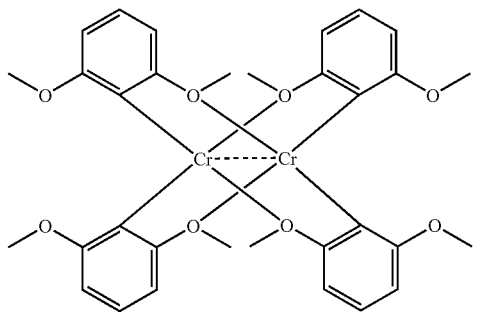

5

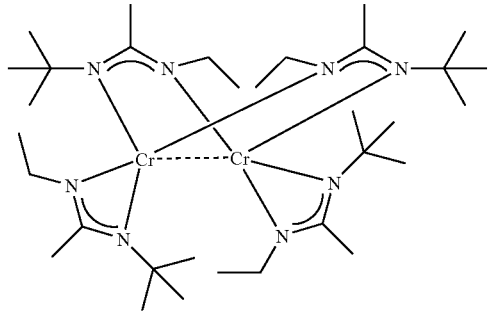

6

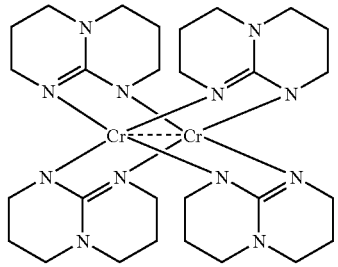

7

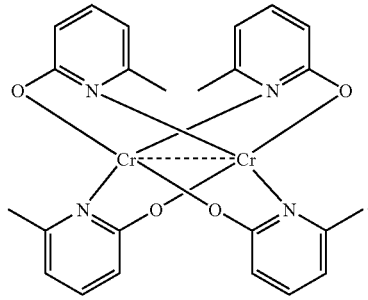

8

13. Process according to claim 12, wherein the solvent is toluene.

14. The process according to claim 13, wherein the process is carried out continuously and the mean residence time of the contacting of ethylene with said catalyst composition is from 1 to 4 hours.

15. The catalyst composition of claim 2, wherein $R_1$, $R_2$, $R_3$, $R_4$, $R_5$, $R_6$ and $R_7$ are selected from the group consisting of chloro, amino, trimethylsilyl, methyl, ethyl, isopropyl, tert-butyl, phenyl, benzyl, tolyl and xylyl and the ligand is selected from the group consisting of $(Ph)_2P$—$N(i-Pr)$—$P(CH_3)$—$N(i-Pr)$—H, $(Ph)_2P$—$N(i-Pr)$—$P(Ph)$—$N(i-Pr)$—H, $(Ph)_2P$—$N(i-Pr)$—$P(Ph)$—$N(Ph)$—H, $(Ph)_2P$—$N(i-Pr)$—$P(Ph)$—$N(tert-butyl)$-H and $(Ph)_2P$—$N(i-Pr)$—$P(Ph)$—$N(CH(CH_3)(Ph))$—H.

16. The catalyst composition of claim 15, further comprising a solvent selected from the group consisting of aromatic hydrocarbons, straight-chain and cyclic aliphatic hydrocarbons, straight-chain olefins and ethers, toluene, benzene, ethyl benzene, cumene, xylenes, mesitylene, hexane, octane, cyclohexane, methylcyclohexane, hexene, heptene, octene, diethylether and tetrahydrofurane, or mixtures thereof.

17. The catalyst composition of claim 15, wherein the activator or co-catalyst is selected from the group comprising trimethyl aluminium, triethyl aluminium, triisopropyl aluminum, triisobutyl aluminium, ethylaluminum sesquichloride, diethylaluminum chloride, ethyl aluminium dichloride and methylaluminoxane (MAO), or mixtures thereof.

18. The catalyst composition of claim 17, wherein the solvent is toluene.

19. The catalyst composition of claim 18, wherein the PNPN or the PNPNP unit in the ligand is part of a ring system.

20. A process for making a catalyst composition, combining at least:
(a) a binuclear chromium(II) complex;
(b) a ligand of the general structure
   (A) $R_1R_2P$—$N(R_3)$—$P(R_4)$—$N(R_5)$—H or
   (B) $R_1R_2P$—$N(R_3)$—$P(R_4)$—$N(R_5)$—$PR_6R_7$,
   Wherein $R_1$, $R_2$, $R_3$, $R_4$, $R_5$, $R_6$ and $R_7$ are independently selected from halogen, amino, trimethylsilyl, $C_1$-$C_{10}$-alkyl, aryl and substituted aryl; and
(c) an activator or co-catalyst.

* * * * *